(12) United States Patent
Baek et al.

(10) Patent No.: US 9,368,414 B2
(45) Date of Patent: Jun. 14, 2016

(54) SEMICONDUCTOR INSPECTING APPARATUS AND METHOD OF INSPECTING AND MANUFACTURING SEMICONDUCTOR DEVICE USING THE SAME

(71) Applicants: Seung Hyeon Baek, Suwon-si (KR); Jaehong Kim, Seoul (KR)

(72) Inventors: Seung Hyeon Baek, Suwon-si (KR); Jaehong Kim, Seoul (KR)

(73) Assignee: SAMSUNG ELECTRONICS CO., LTD., Samsung-ro, Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 14/602,284

(22) Filed: Jan. 22, 2015

(65) Prior Publication Data

US 2015/0270182 A1 Sep. 24, 2015

(30) Foreign Application Priority Data

Mar. 20, 2014 (KR) ........................ 10-2014-0032887

(51) Int. Cl.
*H01L 21/66* (2006.01)
*H01L 21/56* (2006.01)
(Continued)

(52) U.S. Cl.
CPC ............ *H01L 22/12* (2013.01); *G01N 21/9501* (2013.01); *H01L 21/563* (2013.01); *H01L 25/50* (2013.01); *H01L 24/13* (2013.01); *H01L 24/14* (2013.01); *H01L 24/16* (2013.01); *H01L 24/17* (2013.01); *H01L 24/29* (2013.01); *H01L 24/32* (2013.01); *H01L 24/33* (2013.01); *H01L 24/73* (2013.01); *H01L 24/81* (2013.01); *H01L 24/83* (2013.01); *H01L 24/92* (2013.01); *H01L 25/0657* (2013.01); *H01L 25/105* (2013.01);
*H01L 2224/131* (2013.01); *H01L 2224/14131* (2013.01); *H01L 2224/14133* (2013.01);
(Continued)

(58) Field of Classification Search
CPC ......... H01L 21/66; H01L 25/00; H01L 21/78; H01L 23/00; H01L 21/56; G01N 21/95
USPC .................. 438/14, 15, 16, 26, 127; 250/221; 700/109, 110
See application file for complete search history.

(56) References Cited

U.S. PATENT DOCUMENTS 5,982,631 A 11/1999 Bowles et al.
6,310,120 B1 10/2001 Shiobara et al.
(Continued)

FOREIGN PATENT DOCUMENTS

JP 2007-180361 7/2007
JP 2007-250590 9/2007
(Continued)

Primary Examiner — Caleb Henry
(74) Attorney, Agent, or Firm — Muir Patent Law, PLLC

(57) ABSTRACT

A method of manufacturing a semiconductor device includes: preparing a semiconductor device comprising a first substrate, a second substrate disposed on the first substrate, inner terminals disposed between the first and second substrates, and a filling material disposed between the first and second substrates and between the inner terminals; loading the semiconductor device on a stage; irradiating an electromagnetic wave to the filling material in a direction parallel to a top surface of the first substrate by an electromagnetic wave generating unit; and scanning the filling material as the electromagnetic wave generating unit is moved in relation to the stage in a direction along a first side of the semiconductor device while maintaining the irradiating direction of the electromagnetic wave.

20 Claims, 13 Drawing Sheets

(51) Int. Cl.
  *H01L 25/00* (2006.01)
  *G01N 21/95* (2006.01)
  *H01L 23/00* (2006.01)
  *H01L 25/065* (2006.01)
  *H01L 25/10* (2006.01)

(52) U.S. Cl.
  CPC ............... *H01L2224/16227* (2013.01); *H01L 2224/17181* (2013.01); *H01L 2224/2919* (2013.01); *H01L 2224/32225* (2013.01); *H01L 2224/33181* (2013.01); *H01L 2224/73204* (2013.01); *H01L 2224/81801* (2013.01); *H01L 2224/83104* (2013.01); *H01L 2224/92125* (2013.01)

(56) References Cited

U.S. PATENT DOCUMENTS

| | | | |
|---|---|---|---|
| 7,622,311 B1* | 11/2009 | Cha | G06T 7/0006 257/687 |
| 7,705,351 B2 | 4/2010 | Ikebe et al. | |
| 7,776,993 B2* | 8/2010 | Buchwalter | C08G 65/2654 257/789 |
| 8,518,722 B2 | 8/2013 | Chen et al. | |
| 2011/0063606 A1* | 3/2011 | Babiarz | G01N 21/95 356/237.1 |
| 2011/0233762 A1* | 9/2011 | Gruber | H01L 21/486 257/737 |
| 2013/0175701 A1* | 7/2013 | Park | H01L 22/12 257/774 |
| 2015/0357253 A1* | 12/2015 | Babiarz | G01N 21/95 438/7 |

FOREIGN PATENT DOCUMENTS

| | | |
|---|---|---|
| JP | 2009-141213 | 6/2009 |
| JP | 2009-170699 | 7/2009 |
| JP | 2012-112677 | 6/2012 |
| KR | 10-2007-0013478 A | 1/2007 |

* cited by examiner

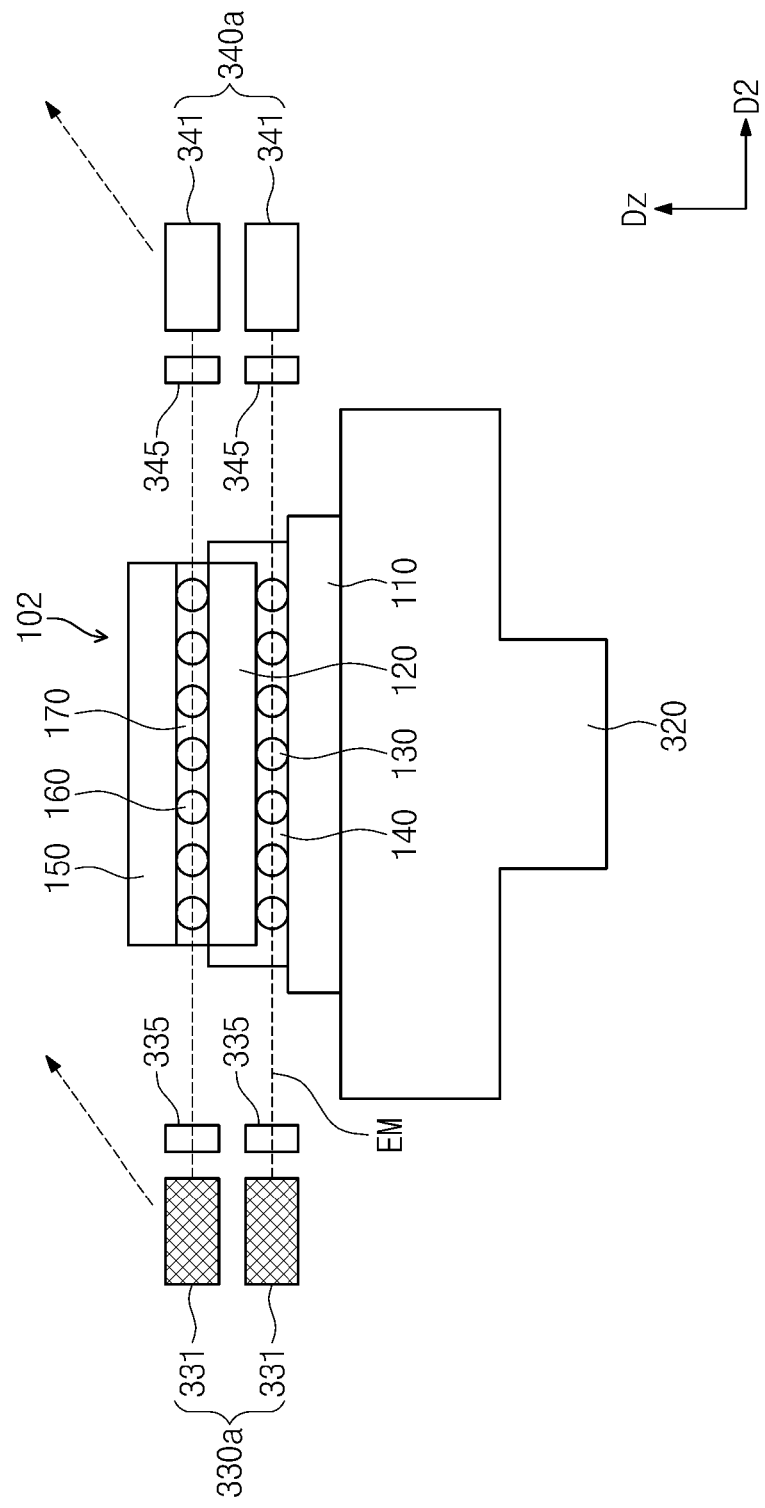

SEMICONDUCTOR INSPECTING APPARATUS AND METHOD OF INSPECTING AND MANUFACTURING SEMICONDUCTOR DEVICE USING THE SAME

CROSS-REFERENCE TO RELATED APPLICATION

This U.S. non-provisional patent application claims priority under 35 U.S.C. §119 to Korean Patent Application No. 10-2014-0032887, filed on Mar. 20, 2014, in the Korean Intellectual Property Office, the disclosure of which is hereby incorporated by reference in its entirety.

BACKGROUND

This disclosure relates to semiconductor inspecting apparatuses and methods of inspecting a semiconductor device and manufacturing a semiconductor device using the same.

Semiconductor devices are widely used in an electronic industry because of their small size, multi-function, and/or low manufacturing costs. A semiconductor device may be manufactured by a semiconductor chip fabrication process of fabricating an integrated circuit on a wafer and a semiconductor packaging process of packaging a semiconductor chip.

The semiconductor chip may be mounted on a printed circuit board using solder balls instead of a conventional wire bonding technique. Generally, a space between solder balls may be filled with an underfill resin.

As semiconductor devices have been highly integrated, spaces between the solder balls have been more and more reduced. Thus, the underfill resin may not sufficiently fill the space between solder balls. In this case, a void may be formed between the solder balls. The void may cause defects of a semiconductor package, so it is important to accurately inspect the void.

SUMMARY

Embodiments of the inventive concepts may provide semiconductor inspecting apparatuses capable of accurately inspecting defects such as a void.

Embodiments of the inventive concepts may also provide methods of inspecting a semiconductor device and methods of manufacturing a semiconductor device using the semiconductor inspecting apparatus.

In one aspect, a method of manufacturing a semiconductor device includes: preparing a first substrate; preparing a second substrate; connecting the first substrate to the second substrate through interconnection terminals disposed between the first substrate and the second substrate; depositing a filling material in spaces between the first substrate and second substrate, the filling material filling spaces between terminals of the interconnection terminals, wherein the first substrate, second substrate, interconnection terminals, and filling material form a semiconductor device; and performing an inspection of the semiconductor device. The inspection includes: loading the semiconductor device on a stage; irradiating an electromagnetic wave to the filling material in a first direction parallel to a top surface of the first substrate by an electromagnetic wave generator; and scanning the filling material by moving the electromagnetic wave generator with respect to the stage along a first side of the semiconductor device while maintaining the first irradiating direction of the electromagnetic wave EM.

In some embodiments, the scanning the filling material includes: moving the electromagnetic wave generator in a second direction perpendicular to the first irradiating direction of the electromagnetic wave.

In some embodiments, the interconnection terminals are arranged in rows and columns, including row-spaces between the rows, and column-spaces between the columns, and scanning the filling material includes scanning the rows and row-spaces by maintaining the first irradiating direction of the electromagnetic wave EM to be parallel to the longitudinal direction of the rows while moving the electromagnetic wave generator with respect to the stage along the side of the semiconductor device.

In one embodiment, the scanning includes using an electromagnetic wave detector in combination with the electromagnetic wave generator to detect electromagnetic wave characteristics as the electromagnetic wave generator moves with respect to the stage along the first side of the semiconductor device.

In some embodiments, the method further includes rotating the stage with respect to the electromagnetic wave generator; and subsequently scanning the filling material by scanning the columns and column-spaces, to detect electromagnetic wave characteristics as the electromagnetic wave generator moves with respect to the stage along a second side of the semiconductor device adjacent to the first side.

The method may additionally include, based on the scanning and subsequent scanning steps, determining whether any voids are included in the filling material. Further, based on the scanning and subsequent scanning steps, the method may determine a two-dimensional location of voids included in the filling material.

In one embodiment, the first substrate is a package substrate, and the second substrate is a chip substrate stacked on the package substrate.

In certain embodiments, the method further includes preparing a third substrate; connecting the third substrate to the second substrate through additional interconnection terminals disposed between the second substrate and the third substrate; and depositing an additional filling material in spaces between the second substrate and third substrate. Performing the inspection of the semiconductor device may further include: irradiating an electromagnetic wave to the additional filling material in the first direction parallel to the top surface of the first substrate by an additional electromagnetic wave generator; and scanning the additional filling material by moving the additional electromagnetic wave generator together with the electromagnetic wave generator.

In one embodiment, the first substrate is a wafer substrate, and after the scanning, the semiconductor device is singulated from the wafer.

In yet another aspect, a method of manufacturing a semiconductor device may include: preparing a semiconductor device comprising a first substrate, a second substrate disposed on the first substrate, inner terminals disposed between the first and second substrates, and a filling material disposed between the first and second substrates and between the inner terminals; loading the semiconductor device on a stage; irradiating an electromagnetic wave to the filling material in a direction parallel to a top surface of the first substrate by an electromagnetic wave generating unit; and scanning the filling material as the electromagnetic wave generating unit is moved in relation to the stage in a direction along a first side of the semiconductor device while maintaining the irradiating direction of the electromagnetic wave.

In some embodiments, the inner terminals may be two-dimensionally arranged along rows and columns when viewed from a plan view, and the filling material may be disposed in row-spaces between the rows and column-spaces between the columns. Scanning the filling material may include: sequentially irradiating the electromagnetic waves into the row-spaces in a direction parallel to the rows and row-spaces as the electromagnetic wave generating unit is moved along the first side of the semiconductor device.

In some embodiments, during the scanning, the electromagnetic wave generating unit is moved in a direction perpendicular to the irradiating direction.

In some embodiments, the method may further include: rotating at least one of the electromagnetic wave generating unit and the stage with respect to a center of a top surface of the stage after sequentially irradiating the electromagnetic waves into the row-spaces; and after the rotation, sequentially irradiating the electromagnetic waves into the column-spaces as the electromagnetic wave generating unit is moved.

In some embodiments, the method includes, based on results of the scanning and the subsequent sequential irradiating steps, determining whether any voids are included in the filling material. The method may additionally include, based on the scanning and subsequent sequential irradiating steps, determining a two-dimensional location of voids included in the filling material.

In certain embodiments, the scanning includes using an electromagnetic wave detecting unit in combination with the electromagnetic wave generating unit to detect electromagnetic wave characteristics as the electromagnetic wave generating unit moves with respect to the stage along the first side of the semiconductor device.

In one aspect, a semiconductor inspecting method may include: providing a stage on which a semiconductor device is loaded, the semiconductor device comprising a first substrate, a second substrate disposed on the first substrate, inner terminals disposed between the first and second substrates, and a filling material disposed between the first and second substrates and between the inner terminals; providing an electromagnetic wave generating unit that irradiates an electromagnetic wave to the filling material disposed between the first and second substrates in a direction parallel to a top surface of the first substrate; and providing an electromagnetic wave detecting unit that detects the irradiated electromagnetic wave. The electromagnetic wave generating unit may scan the filling material as the electromagnetic wave generating unit moves along a movement direction along a first side of the semiconductor device.

In some embodiments, the inner terminals may be two-dimensionally arranged along rows and columns when viewed from a plan view. The filling material may be disposed in row-spaces between the rows and column-spaces between the columns, and the electromagnetic wave generating unit may sequentially irradiate the electromagnetic waves into the row-spaces as it moves. Also, the movement direction may be perpendicular to an irradiating direction of the electromagnetic wave.

In some embodiments, at least one of the electromagnetic wave generating unit and the stage may be rotatable with respect to a center of a top surface of the stage when viewed from a plan view.

In some embodiments, the at least one of the electromagnetic wave generating unit and the stage may be rotated with respect to the center of the top surface of the stage after the electromagnetic wave generating unit sequentially irradiates the electromagnetic waves into the row-spaces, and subsequent to the rotation, the electromagnetic wave generating unit may sequentially irradiate the electromagnetic wave into the column-spaces as it moves.

In some embodiments, the second substrate may include a first sidewall extending in a first direction and a second sidewall extending in a second direction intersecting the first direction. The rows may be parallel to the first sidewall, and the columns may be parallel to the second sidewall.

In some embodiments, the second substrate may include a first sidewall extending in a first direction and a second sidewall extending in a second direction intersecting the first direction, and the rows may be parallel to a third direction that is non-parallel to the first and second sidewalls. In this case, the columns may be parallel to a fourth direction that is non-parallel to the first and second sidewalls and intersects the third direction.

In some embodiments, the semiconductor inspecting method may further include: providing a control system that analyzes detection data obtained from the electromagnetic wave detecting unit to judge whether a void occurs in the filling material or not.

In some embodiments, the electromagnetic wave generating unit and the electromagnetic wave detecting unit may be disposed at both opposite sides of the loaded semiconductor device, respectively, and the electromagnetic wave detecting unit may detect a physical quantity of the electromagnetic wave transmitted through the filling material.

In some embodiments, the electromagnetic wave generating unit and the electromagnetic wave detecting unit may be disposed at one side of the loaded semiconductor device, and the electromagnetic wave detecting unit may detect a physical quantity of the electromagnetic wave that transmits the filling material and is then reflected to be returned through the filling material.

In some embodiments, the electromagnetic wave generating unit may include a plurality of electromagnetic wave generators stacked in a direction perpendicular to a top surface of the stage.

In some embodiments, the semiconductor device may further include second inner terminals disposed on the second substrate, a third substrate disposed on the second inner terminals, and a second filling material disposed between the second and third substrates. The electromagnetic wave generators may irradiate electromagnetic waves to the filling material between the first and second substrates and the second filling material between the second and third substrates at the same time.

In some embodiments, the semiconductor inspecting method may further include: providing a condensing system disposed between the electromagnetic wave generating unit and the loaded semiconductor device. The condensing system may condense the electromagnetic wave.

BRIEF DESCRIPTION OF THE DRAWINGS

The inventive concepts will become more apparent in view of the attached drawings and accompanying detailed description.

FIG. 5B is a cross-sectional view illustrating the semiconductor inspecting apparatus of FIG. 5A, according to one embodiment;

DETAILED DESCRIPTION OF THE EMBODIMENTS

Figure 1:
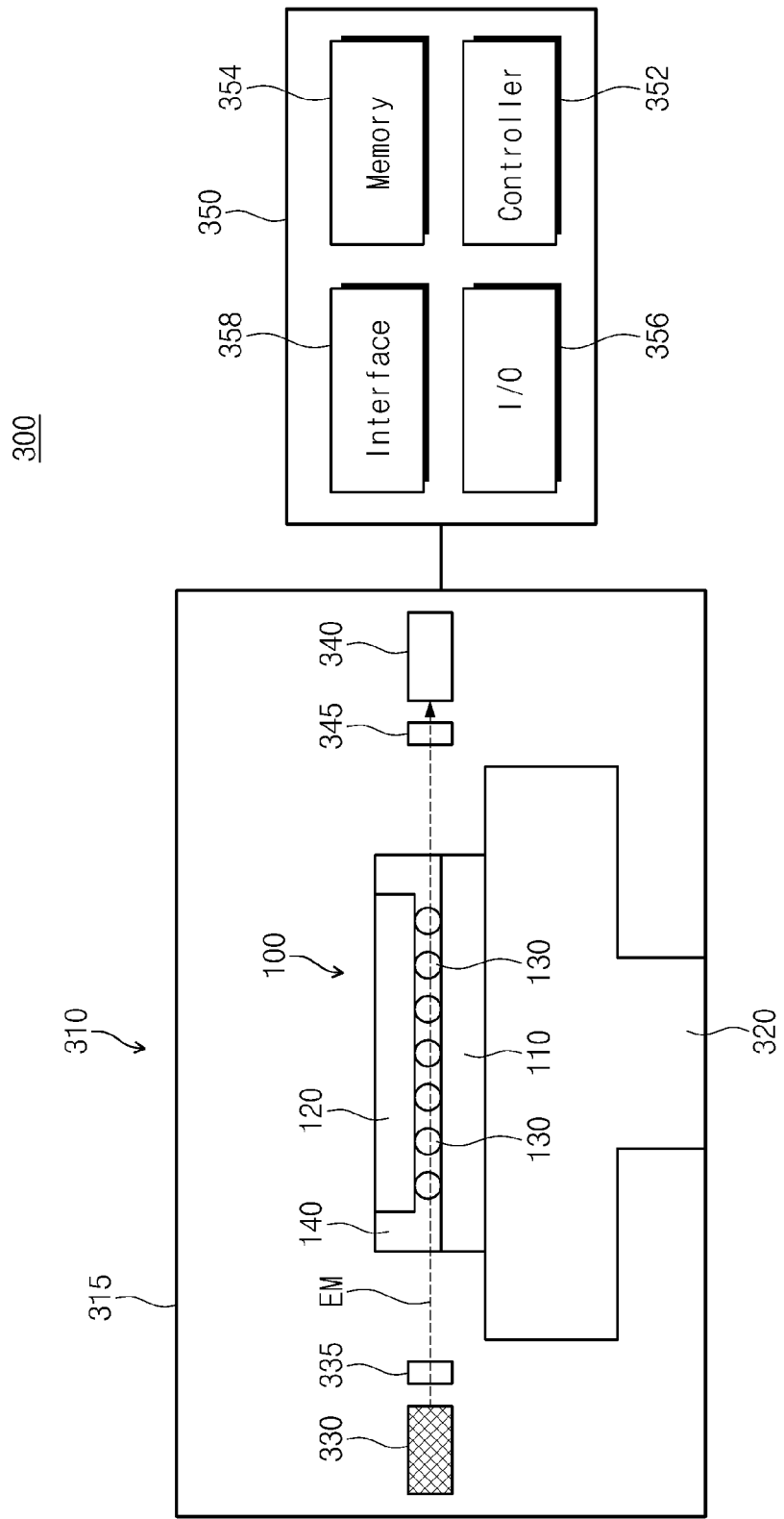
FIG. 1 is a schematic diagram illustrating a semiconductor inspecting apparatus according to example embodiments of the inventive concepts.

The present disclosure will now be described more fully hereinafter with reference to the accompanying drawings, in which exemplary embodiments of the inventive concepts are shown. The advantages and features of the inventive concepts and methods of achieving them will be apparent from the following exemplary embodiments that will be described in more detail with reference to the accompanying drawings. It should be noted, however, that the inventive concepts are not limited to the following exemplary embodiments, and may be implemented in various forms. Accordingly, the exemplary embodiments are provided only to disclose the inventive concepts and let those skilled in the art know the category of the inventive concepts. In the drawings, embodiments of the inventive concepts are not limited to the specific examples provided herein and are exaggerated for clarity.

The terminology used herein is for the purpose of describing particular embodiments only and is not intended to limit the invention. As used herein, the singular terms "a," "an" and "the" are intended to include the plural forms as well, unless the context clearly indicates otherwise. As used herein, the term "and/or" includes any and all combinations of one or more of the associated listed items. It will be understood that when an element is referred to as being "connected" or "coupled" to another element, it may be directly connected or coupled to the other element or intervening elements may be present.

Similarly, it will be understood that when an element such as a layer, region or substrate is referred to as being "on" another element, it can be directly on the other element or intervening elements may be present. In contrast, the term "directly" means that there are no intervening elements. Also, the term "contact" as used herein, refers to a direct contact, or touching, unless the context indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

Additionally, the embodiments in the detailed description will be described with sectional views as ideal exemplary views of the inventive concepts. Accordingly, shapes of the exemplary views may be modified according to manufacturing techniques and/or allowable errors. Therefore, the embodiments of the inventive concepts are not limited to the specific shape illustrated in the exemplary views, but may include other shapes that may be created according to manufacturing processes. Areas exemplified in the drawings have general properties, and are used to illustrate specific shapes of elements. Thus, this should not be construed as limiting the scope of the inventive concepts.

It will be also understood that although the terms first, second, third etc. may be used herein to describe various elements, these elements should not be limited by these terms. Unless the context indicates otherwise, these terms are only used to distinguish one element from another element, for example as a naming convention. Thus, a first element in some embodiments could be termed a second element in other embodiments without departing from the teachings of the present invention. Exemplary embodiments of aspects of the present inventive concepts explained and illustrated herein include their complementary counterparts. The same reference numerals or the same reference designators denote the same elements throughout the specification.

Moreover, exemplary embodiments are described herein with reference to cross-sectional illustrations and/or plane illustrations that are idealized exemplary illustrations. Accordingly, variations from the shapes of the illustrations as a result, for example, of manufacturing techniques and/or tolerances, are to be expected. Thus, exemplary embodiments should not be construed as limited to the shapes of regions illustrated herein but are to include deviations in shapes that result, for example, from manufacturing. For example, an etching region illustrated as a rectangle will, typically, have rounded or curved features. Thus, the regions illustrated in the figures are schematic in nature and their shapes are not intended to limit the scope of example embodiments.

As appreciated by the present inventive entity, devices and methods of forming devices according to various embodiments described herein may be embodied in microelectronic devices such as integrated circuits, wherein a plurality of devices according to various embodiments described herein are integrated in the same microelectronic device. Accordingly, the cross-sectional view(s) illustrated herein may be replicated in two different directions, which need not be orthogonal, in the microelectronic device. Thus, a plan view of the microelectronic device that embodies devices according to various embodiments described herein may include a plurality of the devices in an array and/or in a two-dimensional pattern that is based on the functionality of the microelectronic device.

The devices according to various embodiments described herein may be interspersed among other devices depending on the functionality of the microelectronic device. Moreover, microelectronic devices according to various embodiments described herein may be replicated in a third direction that may be orthogonal to the two different directions, to provide three-dimensional integrated circuits.

Accordingly, the cross-sectional view(s) illustrated herein provide support for a plurality of devices according to various embodiments described herein that extend along two different directions in a plan view and/or in three different directions in a perspective view. For example, when a single terminal is illustrated in a cross-sectional view of a device/ structure, the device/structure may include a plurality of terminals behind it, as would be illustrated by a plan view of the device/structure.

Terms such as "same," "planar," "coplanar," "parallel," or "perpendicular," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to reflect this meaning.

Figure 2:
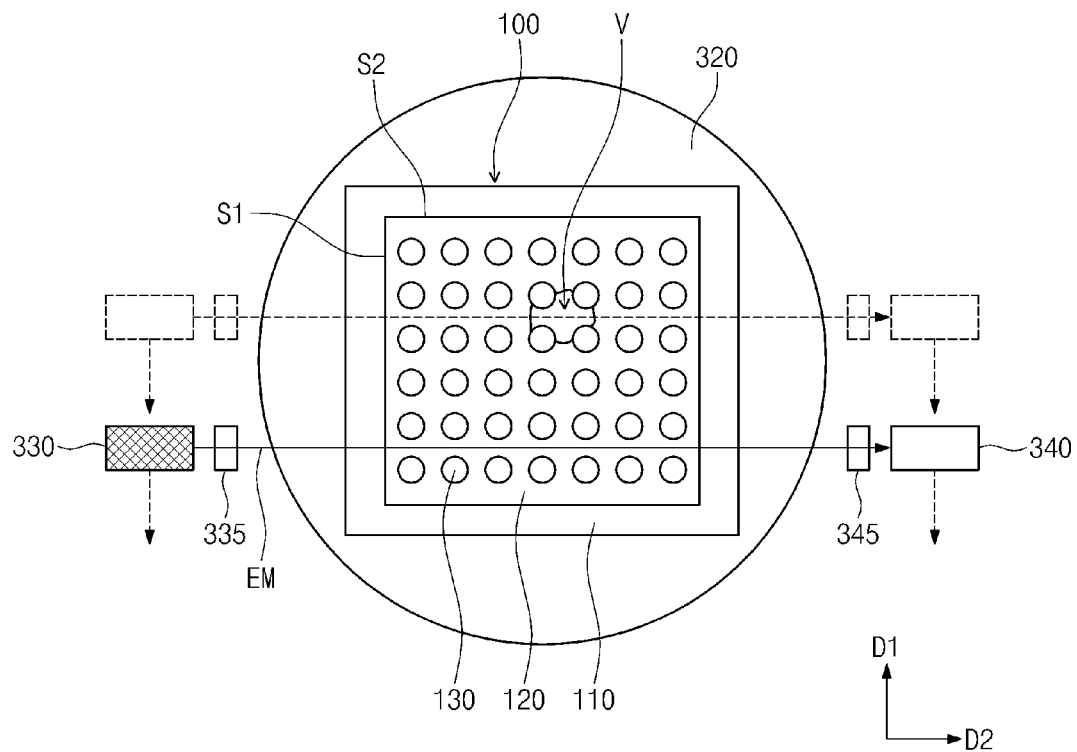
FIGS. 2 and 3 are plan views illustrating a portion of a semiconductor inspecting apparatus according to a first embodiment of the inventive concepts.
Figure 3:
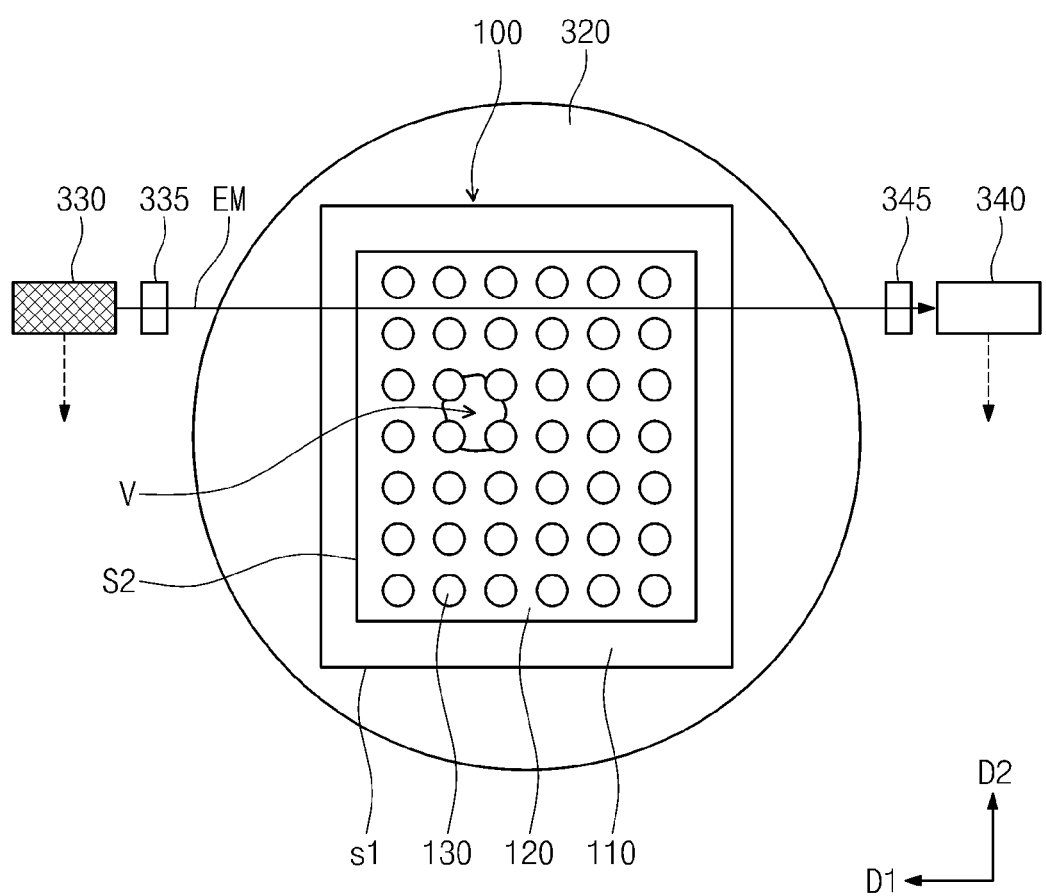

FIG. 1 is a schematic diagram illustrating a semiconductor inspecting apparatus according to example embodiments of the inventive concepts. FIGS. 2 and 3 are plan views illustrating a portion of a semiconductor inspecting apparatus according to a first embodiment of the inventive concepts.

Referring to FIG. 1, a semiconductor inspecting apparatus 300 may include an inspecting system 310 and a control system 350. A semiconductor device 100 may be inspected by the inspecting system 310, and the control system 350 may control operations of the inspecting system 310. In addition, the control system 350 may process data obtained from the inspecting system 310.

The semiconductor device 100 may include a first substrate 110, a second substrate 120 stacked on the first substrate 110, inner terminals 130, and a filling material 140. The inner terminals 130 may be disposed between the first and second substrates 110 and 120. The filling material 140 may be disposed between the first and second substrates 110 and 120 and may fill a space between the inner terminals 130.

The semiconductor device 100 may be, for example, a multi-chip semiconductor device including stacked semiconductor chips. In this case, the first substrate 110 and the second substrate 120 may be a first semiconductor chip and a second semiconductor chip, respectively. For example, each semiconductor chip may include a die formed from a wafer. In this case, at least one of the first and second semiconductor chips may include one or more through-electrodes. The through-electrodes may penetrate the first or second semiconductor chip.

Alternatively, the semiconductor device 100 may be a semiconductor package. For example, the semiconductor device 100 may be a single-chip semiconductor package, a multi-chip semiconductor package, or a package-on-package (PoP). The single-chip semiconductor package may include one semiconductor chip mounted on one package substrate. The multi-chip semiconductor package may include a plurality of semiconductor chips stacked on one package substrate. The PoP device may include semiconductor packages that are sequentially stacked. In this case, the first substrate 110 may be a package substrate or a lower package including at least one lower semiconductor chip. The second substrate 120 may be a semiconductor chip or an upper package including at least one upper semiconductor chip. For example, in one embodiment, the first substrate 110 is a package substrate, and the second substrate 120 is a semiconductor chip, which may be referred to herein as a chip substrate, stacked on the package substrate (e.g., it may be a chip immediately adjacent to the package substrate). In another embodiment, the first substrate 110 is a package substrate of a lower package, and the second substrate 120 is a package substrate of an upper package stacked on the lower package. Inner terminals 100 may be formed between the two package substrates.

Figure 8:
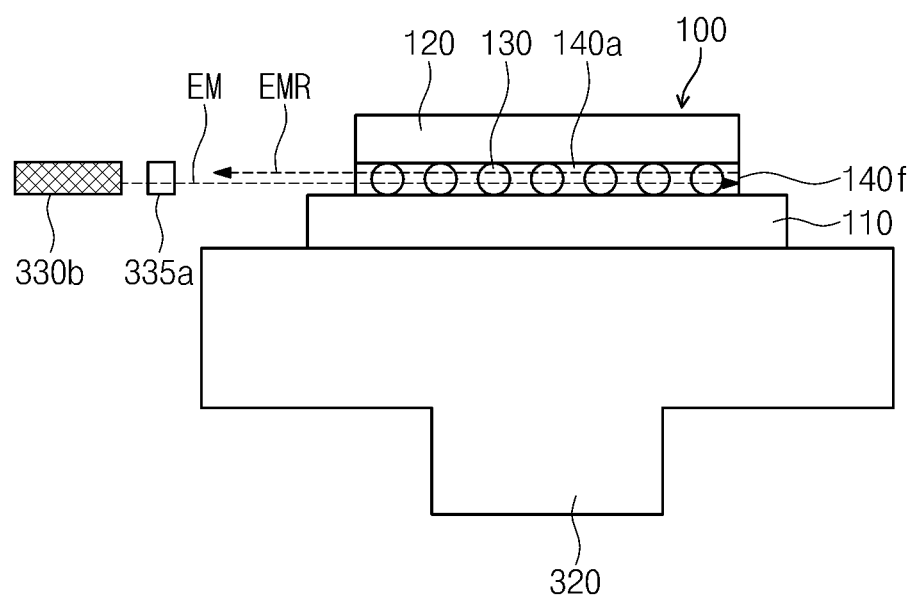
FIG. 8 is a cross-sectional view illustrating the semiconductor inspecting apparatus of FIG. 7, according to one embodiment.

As described above, the filling material 140 may fill the space between the inner terminals 130 and between the first and second substrates 110 and 120. In addition, as illustrated in FIG. 1, in an embodiment where one substrate has a larger area than its adjacent substrate, the filling material 140 may extend to cover a sidewall of the substrate having the smaller area (e.g., the second substrate 120 in FIG. 1). Alternatively, as illustrated in FIG. 8, a filling material 140a may be confinedly disposed in the space between the inner terminals 130 and between the first and second substrates 110 and 120. Thus, in a case such as depicted in FIG. 8, the filling material may extend to outer edges of a smaller substrate of two adjacent substrates stacked on each other (e.g., outer edges of the second substrate 120 of FIG. 8), but may not extend beyond those edges in a lateral direction. In a case where both substrates have the same size (e.g., when viewed in a plan view), the filling material may extend to outer edges of both substrates. In certain embodiments, the filling material 140, also referred to herein as a filler, includes a polymer-based insulating material. For example, the filling material 140 may be an epoxy.

The inspecting system 310 may include a housing 315, a stage 320 (also referred to as a platform), an electromagnetic wave generating unit 330, and an electromagnetic wave detecting unit 340. The stage 320, the electromagnetic wave generating unit 330, and the electromagnetic wave detecting unit 340 may be disposed in the housing 315. The semiconductor device 100 may be loaded on a top surface of the stage 320.

In the embodiment of FIG. 1, the electromagnetic wave generating unit 330 may be an electromagnetic wave generator that irradiates an electromagnetic wave EM in a direction parallel to a top surface of the first substrate 110. The electromagnetic wave generator may include, for example, various circuitry and physical elements configured to generate electromagnetic waves. In certain embodiments, the electromagnetic wave generating unit 330 irradiates the electromagnetic wave EM in a direction parallel to a top surface of the stage 320. The electromagnetic wave generating unit 330 may irradiate the electromagnetic wave EM into the space between the first and second substrates 110 and 120. For example, the electromagnetic wave EM may be irradiated toward a sidewall of the semiconductor device 100. The electromagnetic wave EM may be irradiated to the filling material 140 disposed between the first and second substrates 110 and 120. For example, it may be transmitted at a level at which the filling material 140 is formed, such as a level between the first semiconductor substrate 110 and the second semiconductor substrate 120.

The electromagnetic wave EM may include, for example, at least one of a radio wave, a terahertz wave, or a light wave. The light wave may be one of an infrared ray, a visible ray, an ultraviolet ray, or an X-ray. In some embodiments, the electromagnetic wave EM may be the terahertz wave having excellent transmittance.

The electromagnetic wave detecting unit 340 detects the irradiated electromagnetic wave EM. In more detail, the electromagnetic wave detecting unit 340 may be an electromagnetic wave detector that detects a physical quantity of the electromagnetic wave EM which is transmitted through the filling material 140 at least one time. For example, the physical quantity of the electromagnetic wave EM may be an intensity of the electromagnetic wave EM. The electromagnetic wave detector may include, for example, various circuitry and physical elements configured to detect characteristics of electromagnetic waves, such as the intensity.

In some embodiments, a first condensing system 335, also described as an electromagnetic wave condenser may be disposed between the electromagnetic wave generating unit 330 and the loaded semiconductor device 100. The first condensing system 335 is adjacent to the electromagnetic wave generating unit 330. The first condensing system 335 condenses the electromagnetic wave EM irradiated from the electromagnetic wave generating unit 330, so the spread of the electromagnetic wave EM may be reduced or minimized. As such, the rectilinear propagation of the electromagnetic wave EM may be improved. In some embodiments, the first condensing system 335 may be an optical system including at least one lens. However, the inventive concepts are not limited thereto. The first condensing system 335 may be realized as a system condensing the radio wave or the terahertz wave. The first condensing system 335 may be combined with the electromagnetic wave generating unit 330, and thus, the first condensing system 335 and the electromagnetic wave generating unit 330 may be moved together. The first condensing system 335 and electromagnetic wave generating unit 330 may be collectively referred to as an electromagnetic wave transmitter or electromagnetic wave transmission system.

In some embodiments, a second condensing system 345 may be disposed between the electromagnetic wave detecting unit 340 and the loaded semiconductor device 100 and may be adjacent to the electromagnetic wave detecting unit 340. The second condensing system 345, also described as an electromagnetic wave condenser, may condense the electromagnetic wave EM transmitted through the filling material 140 and may then transfer the condensed electromagnetic wave EM to the electromagnetic wave detecting unit 340. In some embodiments, the second condensing system 345 may be an optical system including at least one lens. However, the inventive concepts are not limited thereto. The second condensing system 345 may be realized as a system condensing the radio wave or the terahertz wave. The second condensing system 345 may be combined with the electromagnetic wave detecting unit 340, so the second condensing system 345 and the electromagnetic wave detecting unit 340 may be moved together. The second condensing system 345 and electromagnetic wave detecting unit 340 may be collectively referred to as an electromagnetic wave receiver or electromagnetic wave receiving system.

The control system 350 may control operations of the stage 320, the electromagnetic wave generating unit 330, and the electromagnetic wave detecting unit 340. The control system 350 may also control the movement of one or more of the electromagnetic wave generating unit 330, the first condensing system 335, the electromagnetic wave detecting unit 340, the second condensing system 345, and the stage 320. The control system 350 may include a controller 352, a memory device 354, an input/output (I/O) unit 356, and an interface unit 358. The controller 352 may process detection data obtained from the electromagnetic wave detecting unit 340. In addition, the controller 352 may analyze the processed data. The memory device 354 may store at least one of the detection data, the processed data, or the analyzed data. Additionally, the memory device 354 may store commands or program data for controlling operations of the inspecting system 310. The I/O unit 356 may include a display device for displaying the data. Additionally, the I/O unit 356 may further include an input device, such as at least one of a keyboard, a keypad, or a mouse. The inspecting system 310 and the control system 350 may exchange data signals and control signals with each other through the interface unit 358. The interface unit 358 may operate, for example, by wireless or cable. For example, the interface unit 358 may include an antenna for wireless communication or a transceiver for cable communication. Each of the controller 352, the memory 354, the I/O unit 356, and the interface 358 may be formed of various hardware and/or software components.

The electromagnetic wave generating unit 330 may scan the filling material 140 between the first and second substrates 110 and 120 as the electromagnetic wave generating unit 330 moves in a direction perpendicular to an irradiating direction of the electromagnetic wave EM. This will be described with reference to FIGS. 2 and 3.

Referring to FIGS. 1, 2, and 3, in one embodiment, the inner terminals 130 of the semiconductor device 100, also referred to as interconnection terminals, may be two-dimensionally arranged along rows and columns when viewed from a plan view. Row-spaces are defined between the rows. As such, the rows and the row-spaces are alternately arranged in a direction perpendicular to a longitudinal direction of the row. Column-spaces are defined between the columns. Thus, the columns and the column-spaces are alternately arranged in a direction perpendicular to a longitudinal direction of the column. The space between the first and second substrates 110 and 120 and between the inner terminals 130 includes the row-spaces and the column-spaces. As such, the filling material 140 may be disposed in the row-spaces and the column-spaces. The inner terminals 130 may be, for example, solder balls or solder bumps.

The electromagnetic wave generating unit 330 may irradiate the electromagnetic wave EM to the filling material 140 disposed in the row-space along the longitudinal direction of the row. When viewed from a plan view, the electromagnetic wave generating unit 330 may scan the filling material 140 as it continues to move in the direction perpendicular to the irradiating direction of the electromagnetic wave EM. In more detail, the electromagnetic wave generating unit 330 may sequentially irradiate the electromagnetic wave EM into the row-spaces as it continues to move in the direction perpendicular to the irradiating direction of the electromagnetic wave EM. Note that while one embodiment describes the electromagnetic wave generating unit 330 as moving in a direction perpendicular to the irradiating direction of the electromagnetic wave EM, the same results may be obtained so long as the irradiating direction of the electromagnetic wave EM is maintained to be in a direction parallel to the longitudinal direction of the rows as the electromagnetic wave generating unit 330 is moved to consecutively traverse the rows (e.g., as it moves along a side of the semiconductor device 100). In some embodiments, such as shown in FIG. 2, the electromagnetic wave generating unit 330 is moved in a direction perpendicular to the irradiating direction of the electromagnetic wave EM to achieve this result. In other embodiments, however, the electromagnetic wave generating unit 330 may be moved in a direction, for example, angled with respect to the side of the semiconductor device 100 as it moves along the side of the semiconductor device, while the irradiating direction of the electromagnetic wave EM stays the same.

In some embodiments, as illustrated in FIGS. 1 to 3, the loaded semiconductor device 100 may be disposed between the electromagnetic wave generating unit 330 and the electromagnetic wave detecting unit 340. For example, the electromagnetic wave detecting unit 340 may be opposite to the electromagnetic wave generating unit 330 with the loaded semiconductor device 100 therebetween. Thus, the electromagnetic wave detecting unit 340 may detect physical characteristics, such as the physical quantity, of the electromagnetic wave EM transmitted through the filling material 140. As the electromagnetic wave detecting unit 340 moves along with the electromagnetic wave generating unit 330, it may intermittently or continuously detect the physical quantity of the electromagnetic wave EM, in a sequence according to the consecutive rows and row-spaces.

In some embodiments, the irradiation of the electromagnetic wave EM may be interrupted when the electromagnetic wave generating unit 330 passes by each row, resulting in intermittent detection. Alternatively, the electromagnetic wave EM may be continuously irradiated when the electromagnetic wave generating unit 330 passes by each row. In this case, the electromagnetic wave EM may be reflected by the inner terminal 130, so the electromagnetic wave detecting unit 340 may detect a substantially zero physical quantity of the electromagnetic wave EM.

The detected physical quantity of the electromagnetic wave EM transmitted through the filling material 140 not having a defect (e.g., a void V) is different from the detected physical quantity of the electromagnetic wave EM transmitted through the filling material 140 having the defect. The void V may be, for example, an empty region in which the filling material 140 does not exist. For example, since the electromagnetic wave EM may be reflected by a boundary of the void V, the detected physical quantity (e.g., a detected intensity) of the electromagnetic wave EM transmitted through the void V may be less than the detected physical quantity (e.g., a detected intensity) of the electromagnetic wave EM transmitted through the filling material 140 not having the void V. As a result, it is possible to confirm whether the void V exists in the filling material 140 or not by a difference between the detected physical quantities. The controller 352 of the control system 350 may compare the detected physical quantities with each other.

As illustrated in FIG. 2, the second substrate 120 of the semiconductor device 100 may include a first sidewall S1 extending in a first direction D1 and a second sidewall S2 extending in a second direction D2 different from the first direction D1. The second direction D2 may be perpendicular to the first direction D1. In some embodiments, the rows of the inner terminals 130 may be parallel to the second sidewall S2, and the columns of the inner terminals 130 may be parallel to the first sidewall S1. In this case, the electromagnetic wave generating unit 330 may face the first sidewall S1, and the irradiating direction of the electromagnetic wave EM may be parallel to the second direction D2. The electromagnetic wave generating unit 330 may move along the first sidewall S1 to scan the filling material 140. Though rows and columns are described herein with respect to certain examples, the terms may be used interchangeably to refer to different directions perpendicular to each other in which inner terminals 130 are arranged.

In a plan view, at least one of the electromagnetic wave generating unit 330 and the stage 320 may be rotated with respect to a center of the top surface of the stage 320. In some embodiments, the electromagnetic wave generating unit 330 may be rotated along the circumference of the stage 320 with respect to the center of the top surface of the stage 320. In other embodiments, the electromagnetic wave generating unit 330 may be fixed, and the stage 320 may be rotated. In still other embodiments, the electromagnetic wave generating unit 330 and the stage 320 may be respectively rotated in opposite directions with respect to the center of the top surface of the stage 320. After the rotating operation, the electromagnetic wave detecting unit 340 may also be opposite to the electromagnetic wave generating unit 330. As such, the electromagnetic wave detecting unit 340 may move or be fixed together with the electromagnetic wave generating unit 330.

As illustrated in FIG. 3, at least one of the electromagnetic wave generating unit 330 and the stage 320 may be rotated, so an irradiating direction of the electromagnetic wave EM of the electromagnetic wave generating unit 330 may be parallel to the columns of the inner terminals 130. For example, the electromagnetic wave generating unit 330 may face the second sidewall S2 of the second substrate 120.

After the rotating operation, the electromagnetic wave generating unit 330 may scan the filling material 140 disposed in the column-spaces as it moves in a direction (e.g., in the second direction D2) perpendicular to the longitudinal direction of the column.

As a result, a two-dimensional coordinates of the void V may be obtained by the two scanning processes described above. In addition, the rotation described above allows for the detection of voids that may be hidden behind an inner terminal along one direction. For example, after the rotation, the void may be detected as being above or below the inner terminal, from a plan view.

According to the semiconductor inspecting apparatus 300 mentioned above, the electromagnetic wave generating unit 330 irradiates the electromagnetic wave EM between the first and second substrates 110 and 120 to inspect the filling material 140. As a result, the electromagnetic wave generating unit 330 directly irradiates the electromagnetic wave EM to the filling material 140, so reliability of the inspection may be improved.

Additionally, the electromagnetic wave generating unit 330 scans the filling material 140 as it moves. Thus, the semiconductor inspecting apparatus 300 may inspect various-sized semiconductor devices. In other words, a moving distance of the electromagnetic wave generating unit 330 in the scanning process may be controlled, so various-sized semiconductor devices may be inspected. As a result, the semiconductor inspecting apparatus 300 may have a high degree of freedom for a size of the semiconductor device.

Moreover, since at least one of the electromagnetic wave generating unit 330 and the stage 320 is rotatable, the two-dimensional coordinates of the void V may be obtained. Thus, the void V may be more accurately and precisely inspected.

In the embodiment described above, the rows of the inner terminals 130 may be parallel to the first sidewall S1 of the second substrate 120. Alternatively, the inner terminals 130 may be arranged differently from the arrangement state illustrated in FIGS. 2 and 3. One example of this will be described with reference to FIG. 4.

Figure 4:
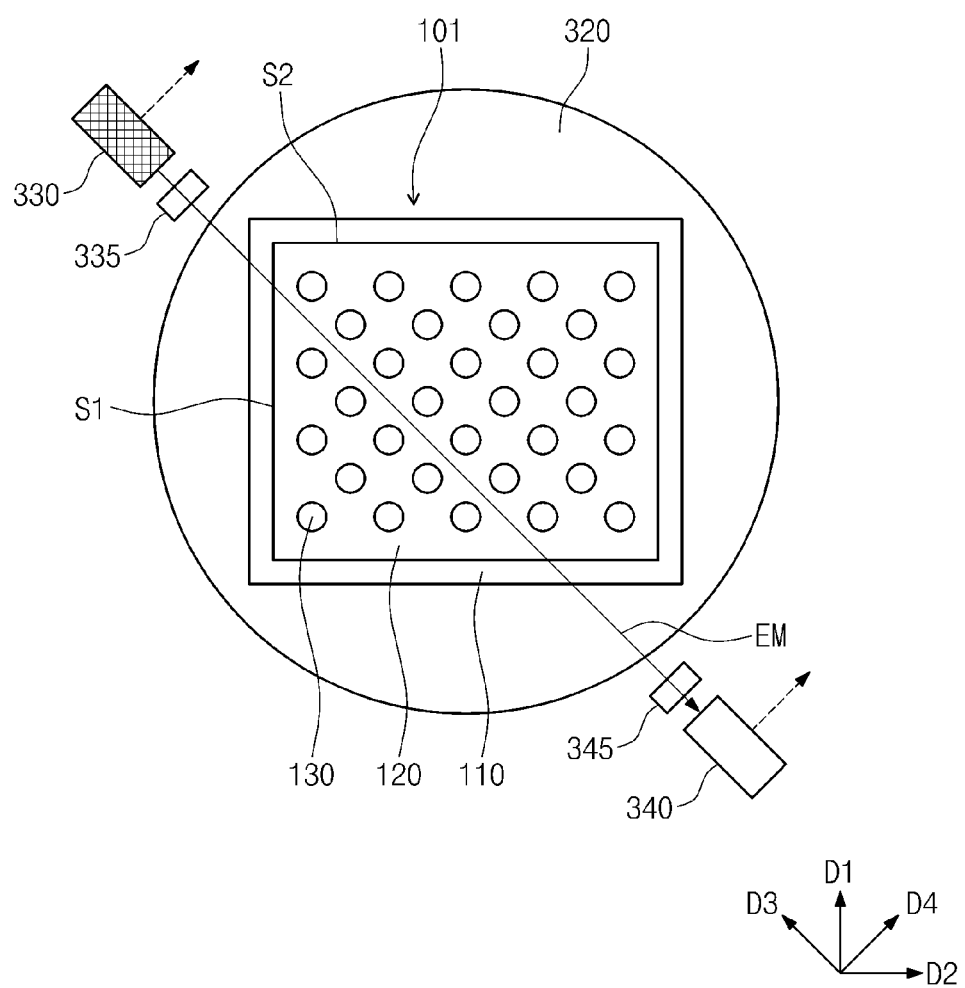
FIG. 4 is a plan view illustrating another arrangement of inner terminals of FIGS. 2 and 3, according to one embodiment.

FIG. 4 is a plan view illustrating another arrangement of inner terminals of FIGS. 2 and 3.

Referring to FIG. 4, rows of inner terminals 130 included in a semiconductor device 101 may be parallel to a third direction D3 that is non-parallel to the first and second sidewalls S1 and S2 of the second substrate 120 of the semiconductor device 101 when viewed from a plan view. Thus, row-spaces between the rows may also be parallel to the third direction D3. Columns of the inner terminals 130 may be parallel to a fourth direction D4 intersecting the third direction D3. Thus, column-spaces between the columns may also be parallel to the fourth direction D4. The fourth direction D4 is non-parallel to the first and second sidewalls S1 and S2. In some embodiments, the fourth direction D4 may be perpendicular to the third direction D3. In this case, some of the inner terminals 130 may be arranged in the first direction D1 to constitute a first line and a second line adjacent to the first line. The inner terminals 130 constituting the first and second lines may be arranged in a zigzag form along the first direction D1.

In the event that the inner terminals 130 are arranged as illustrated in FIG. 4, the electromagnetic wave generating unit 330 may irradiate the electromagnetic wave EM in the third direction D3. In more detail, the electromagnetic wave generating unit 330 may scan the filling material 140 disposed in the row-spaces as it moves in a direction perpendicular to the third direction D3. Next, at least one of the electromagnetic wave generating unit 330 and the stage 320 may be rotated. The electromagnetic wave generating unit 330 may irradiate the electromagnetic wave EM in the fourth direction D4 after the rotating operation. In other words, the electromagnetic wave generating unit 330 may scan the filling material 140 disposed in the column-spaces as it moves in a direction perpendicular to the fourth direction D4.

Next, other embodiments of the inventive concepts will be described with reference to the drawings. Each of semiconductor inspecting apparatuses in the following embodiments includes the control system 350 of FIG. 1. For example, each of the semiconductor inspecting apparatuses in the following embodiments may have an inspecting system different from the inspecting system 310 of the semiconductor inspecting apparatus 300 illustrated in FIGS. 1 to 3. The control system 350 may be the same system in the different embodiments, or a similar system including similar components, but may be programmed differently depending on the different inspecting systems 310 being used. For the purpose of ease and convenience in explanation, differences between the first embodiment and the following embodiments will be mainly described hereinafter.

Figure 5A:
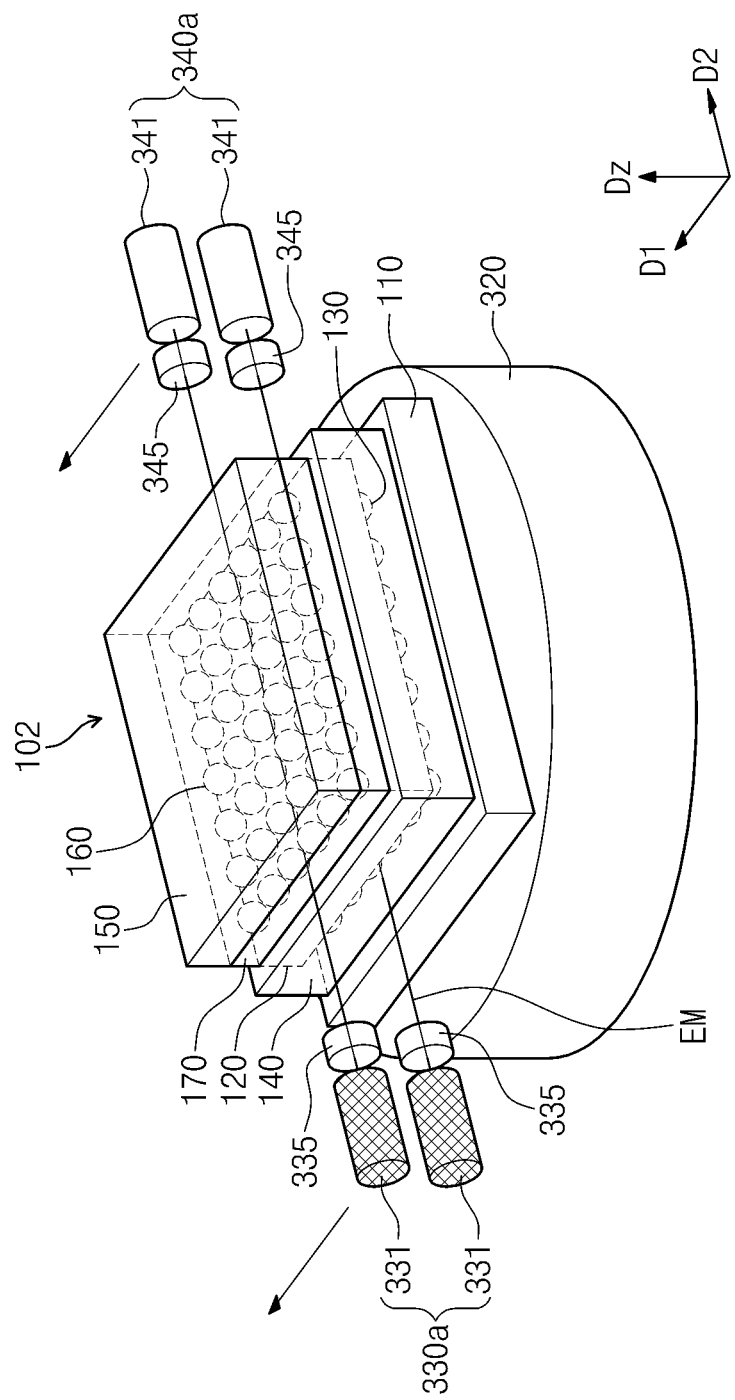
FIG. 5A is a perspective view illustrating a portion of a semiconductor inspecting apparatus according to a second embodiment of the inventive concepts.

FIG. 5A is a perspective view illustrating a portion of a semiconductor inspecting apparatus according to a second embodiment of the inventive concepts. FIG. 5B is a cross-sectional view illustrating the semiconductor inspecting apparatus of FIG. 5A.

Referring to FIGS. 5A and 5B, an electromagnetic wave generating unit 330a according to the present embodiment may include a plurality of electromagnetic wave generators 331 stacked along a direction Dz perpendicular to the top surface of the stage 320. The electromagnetic wave generators 331 may be combined with each other and may move together. Likewise, an electromagnetic wave detecting unit 340a according to the present embodiment may include a plurality of electromagnetic wave detectors 341 stacked along the perpendicular direction Dz. The electromagnetic wave detectors 341 may be combined with each other and may move together.

In some embodiments, a semiconductor device 102 may further include a third substrate 150 stacked on the second substrate 120. In addition, the semiconductor device 102 may further include second inner terminals 160 disposed between the second and third substrates 120 and 150 and a second filling material 170 filling a space between the second inner terminals 160 between the second and third substrates 120 and 150. The third substrate 150 may be, for example, a semiconductor chip or a semiconductor package. The second filling material 170 may be formed, for example, of a polymer-based insulating material. For example, the second filling material 170 may be an epoxy.

The electromagnetic wave generators 331 may irradiate electromagnetic waves EM to the filling material 140 disposed between the first and second substrates 110 and 120 and the second filling material 170 disposed between the second and third substrates 120 and 150, respectively. In some embodiments, the electromagnetic wave generators 331 may irradiate the electromagnetic waves EM at the same time. The electromagnetic wave generating unit 330a including the electromagnetic wave generators 331 may scan the filling material 140 and the second filling material 170 at the same time as it moves in a direction (e.g., the first direction D1) that is perpendicular to the irradiating direction of the electromagnetic waves EM and is parallel to the top surface of the first substrate 110.

After first sidewalls of the filling materials 140 and 170 are scanned, at least one of the electromagnetic wave generating unit 330a and the stage 320 may be rotated and then second sidewalls of the filling materials 140 and 170 may be scanned.

In FIGS. 5A and 5B, two substrates 120 and 150 are sequentially stacked on the first substrate 110. However, the inventive concepts are not limited thereto. Two or more substrates may be stacked on the first substrate 110. For example, the semiconductor device 102 may include a base substrate, a plurality of inner terminal groups and a plurality of upper substrates alternately stacked on the base substrate, and a plurality of filling materials. The base substrate may correspond to the first substrate 100, and the upper substrates may include the second and third substrates 120 and 150. Each of the inner terminal groups includes a plurality of inner terminals. Thus, the first inner terminals 130 may constitute one inner terminal group, and the second inner terminals 160 may constitute another inner terminal group. Each of the filling materials may fill a space between the inner terminals of each of the inner terminal groups. The filling materials 140 and 170 are included in the plurality of filling materials. The electromagnetic wave generators 331 may respectively irradiate the electromagnetic waves EM to corresponding ones of the filling materials.

Meanwhile, the semiconductor device 100 of FIG. 1 may also be inspected using the semiconductor inspecting apparatus according to the embodiment shown in FIGS. 5A and 5B. In this case, one electromagnetic wave generator (e.g. one of the generators 331) corresponding to the filling material 140 may be used, but another electromagnetic wave generator may not be operated.

Figure 6:
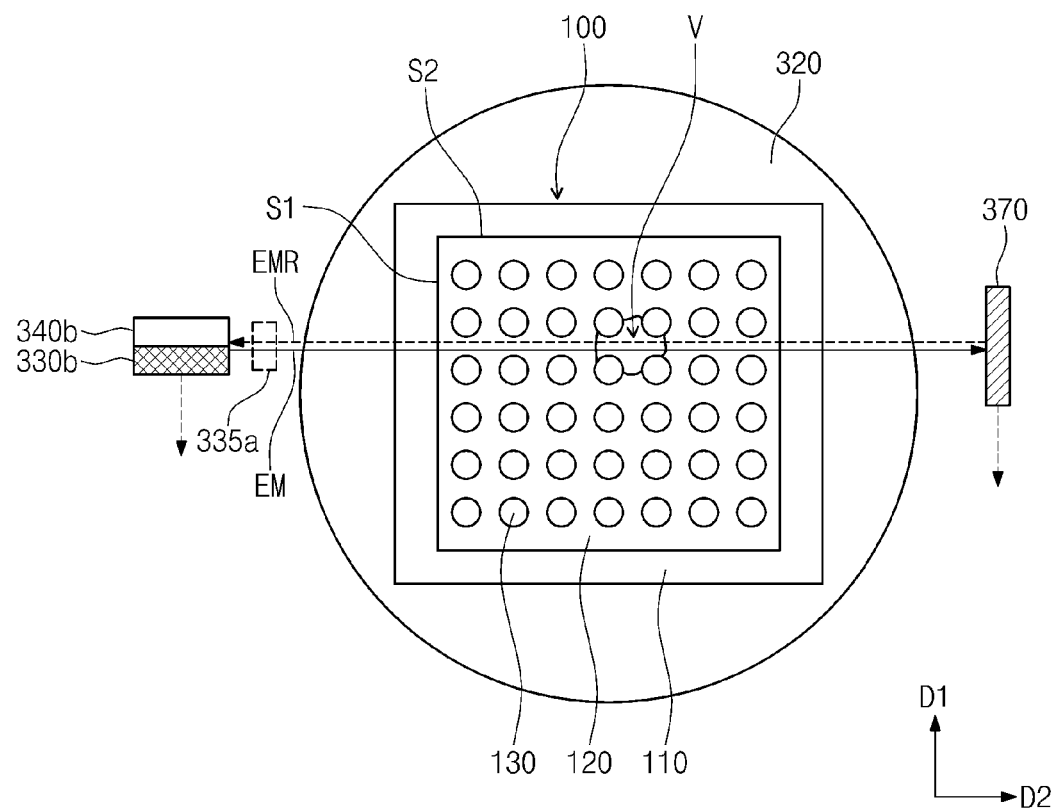
FIG. 6 is a plan view illustrating a portion of a semiconductor inspecting apparatus according to a third embodiment of the inventive concepts.

FIG. 6 is a plan view illustrating a portion of a semiconductor inspecting apparatus according to a third embodiment of the inventive concepts.

Referring to FIG. 6, both an electromagnetic wave generating unit 330b and an electromagnetic wave detecting unit 340b may be disposed at one side of the loaded semiconductor device 100. In some embodiments, the electromagnetic wave generating unit 330b and the electromagnetic wave detecting unit 340b may be combined with each other. Collectively, throughout the various embodiments, the combination of the electromagnetic wave generating unit and the electromagnetic wave detecting unit may be referred to as an electromagnetic wave generating/detection unit. Similarly, the combination of an electromagnetic wave transmission system and an electromagnetic wave receiving system may be referred to as an electromagnetic wave transmission/receiving system.

In the present embodiment, a reflecting plate 370 may be opposite to the electromagnetic wave generating unit 330b and the electromagnetic wave detecting unit 340b. Here, the loaded semiconductor device 100 may be disposed between the reflecting plate 370 and the combined structure of the electromagnetic wave generating unit 330b and the electromagnetic wave detecting unit 340b. The reflecting plate 370 may be formed of a metal or may be a mirror.

The electromagnetic wave generating unit 330b irradiates an electromagnetic wave EM to the filling material 140 disposed between the first and second substrates 110 and 120. The electromagnetic wave EM passes through the filling material 140 and is then reflected by the reflecting plate 370. The reflected electromagnetic wave EMR is returned through the filling material 140. The electromagnetic wave detecting unit 340b detects a physical quantity of the returned electromagnetic wave EMR.

In the present embodiment, if the electromagnetic wave EM passes through the void V, the electromagnetic wave detecting unit 340b detects the physical quantity of the electromagnetic wave EMR transmitted through the void V twice. Thus, a variation amount of the physical quantity caused by the void V may increase, so resolution of the void V may be improved.

A condensing system 335a may be disposed between the loaded semiconductor device 100 and the combined structure of the electromagnetic wave generating unit 330b and the electromagnetic wave detecting unit 340b. The condensing system 335a may condense the electromagnetic wave EM irradiated from the electromagnetic wave generating unit 330b and may also condense the electromagnetic wave EMR returned to the electromagnetic wave detecting unit 340b.

Figure 7:
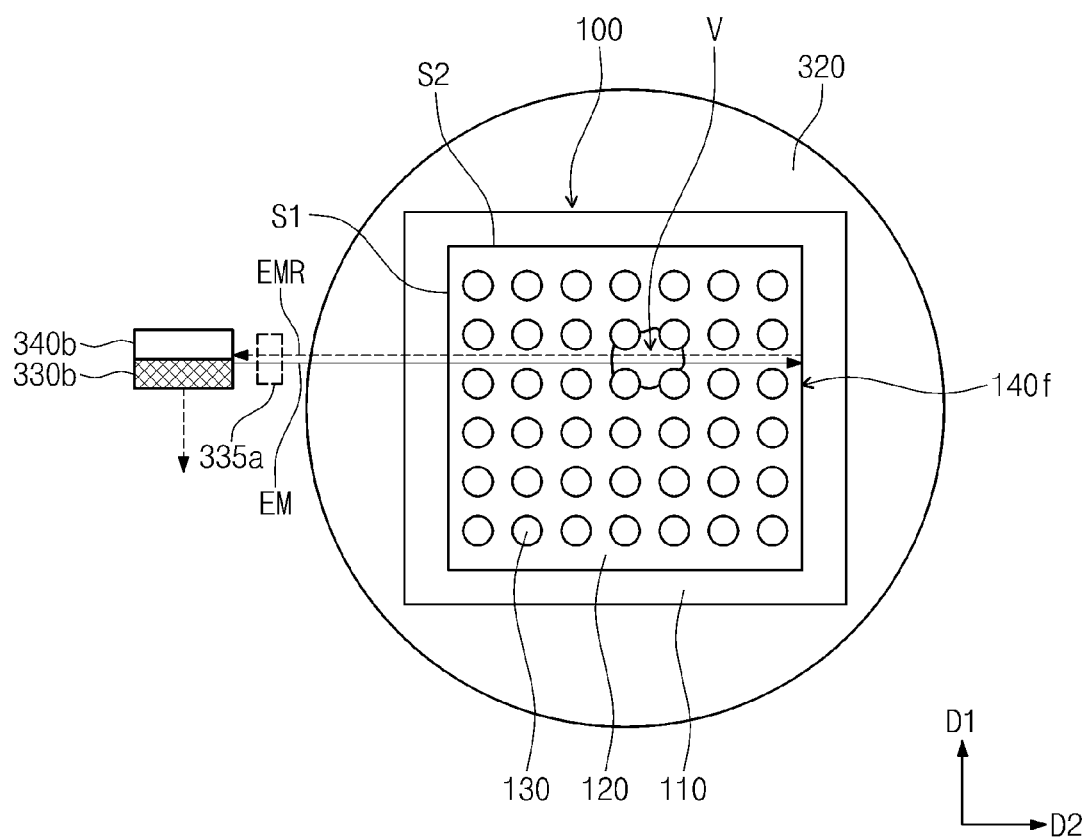
FIG. 7 is a plan view illustrating a portion of a semiconductor inspecting apparatus according to a fourth embodiment of the inventive concepts.

FIG. 7 is a plan view illustrating a portion of a semiconductor inspecting apparatus according to a fourth embodiment of the inventive concepts. FIG. 8 is a cross-sectional view illustrating the semiconductor inspecting apparatus of FIG. 7.

Referring to FIGS. 7 and 8, a semiconductor inspecting apparatus according to the present embodiment may be similar to the semiconductor inspecting apparatus of FIG. 6. However, the semiconductor inspecting apparatus according to the present embodiment may not use the reflecting plate 370 of the semiconductor inspecting apparatus of FIG. 6.

A filling material 140a between the first and second substrates 110 and 120 may have a first sidewall adjacent to the semiconductor inspecting apparatus generating and detecting units 330b and 340b and a second sidewall 140f opposite to the first sidewall. The semiconductor inspecting apparatus according to the present embodiment may use the second sidewall 140f of the filling material 140a as a reflecting surface. In more detail, the electromagnetic wave EM is irradiated from the electromagnetic wave generating unit 330b to the sidewall of the semiconductor device 100 to pass through the filling material 140a, and the electromagnetic wave EM is then reflected by the second sidewall 140f of the filling material 140a. The reflected electromagnetic wave EMR re-passes through the filling material 140a and is then inputted to the electromagnetic wave detecting unit 340b.

In the aforementioned embodiments, the top surface of the stage 320 may have a circular shape. However, the inventive concepts are not limited thereto.

Figure 9:
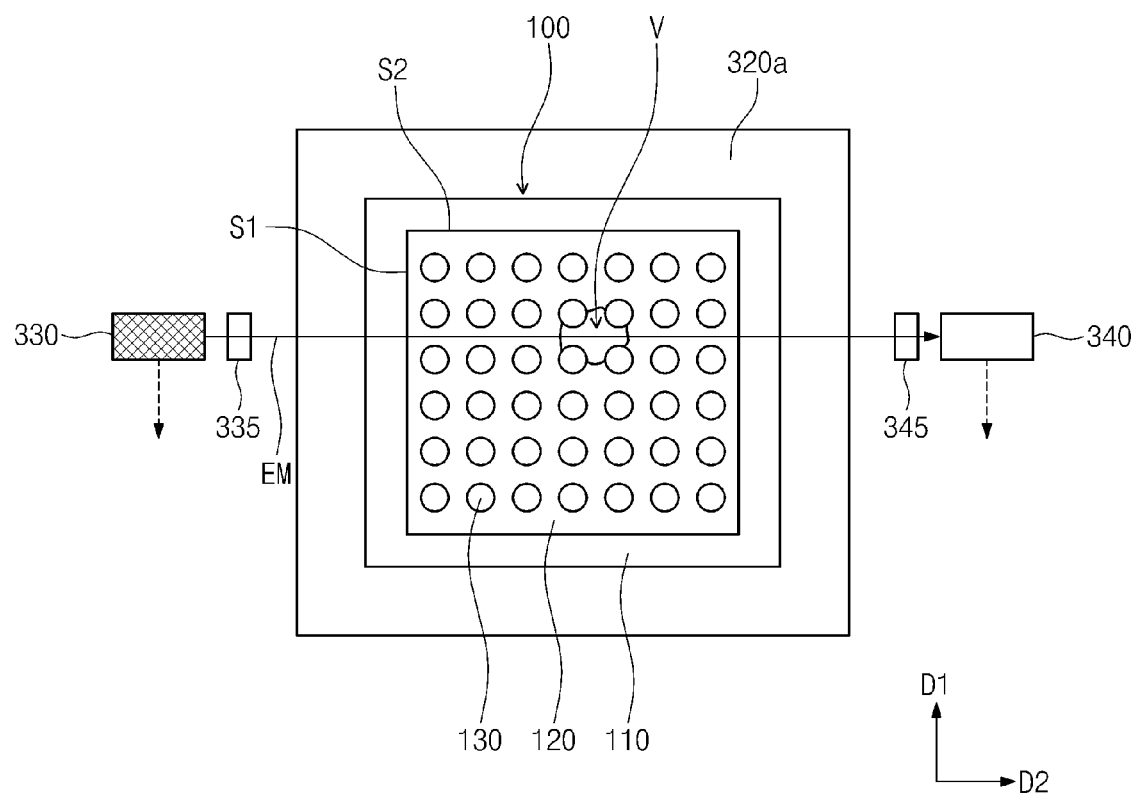
FIG. 9 is a plan view illustrating a portion of a semiconductor inspecting apparatus according to a fifth embodiment of the inventive concepts.

FIG. 9 is a plan view illustrating a portion of a semiconductor inspecting apparatus according to a fifth embodiment of the inventive concepts.

Referring to FIG. 9, a top surface of a stage 320a according to the present embodiment may have a polygonal shape. In some embodiments, the top surface of the stage 320a may have a quadrilateral shape, as illustrated in FIG. 9. Alternatively, the top surface of the stage 320a may have another polygonal shape such as a hexagonal shape or an octagonal shape.

Figure 10:
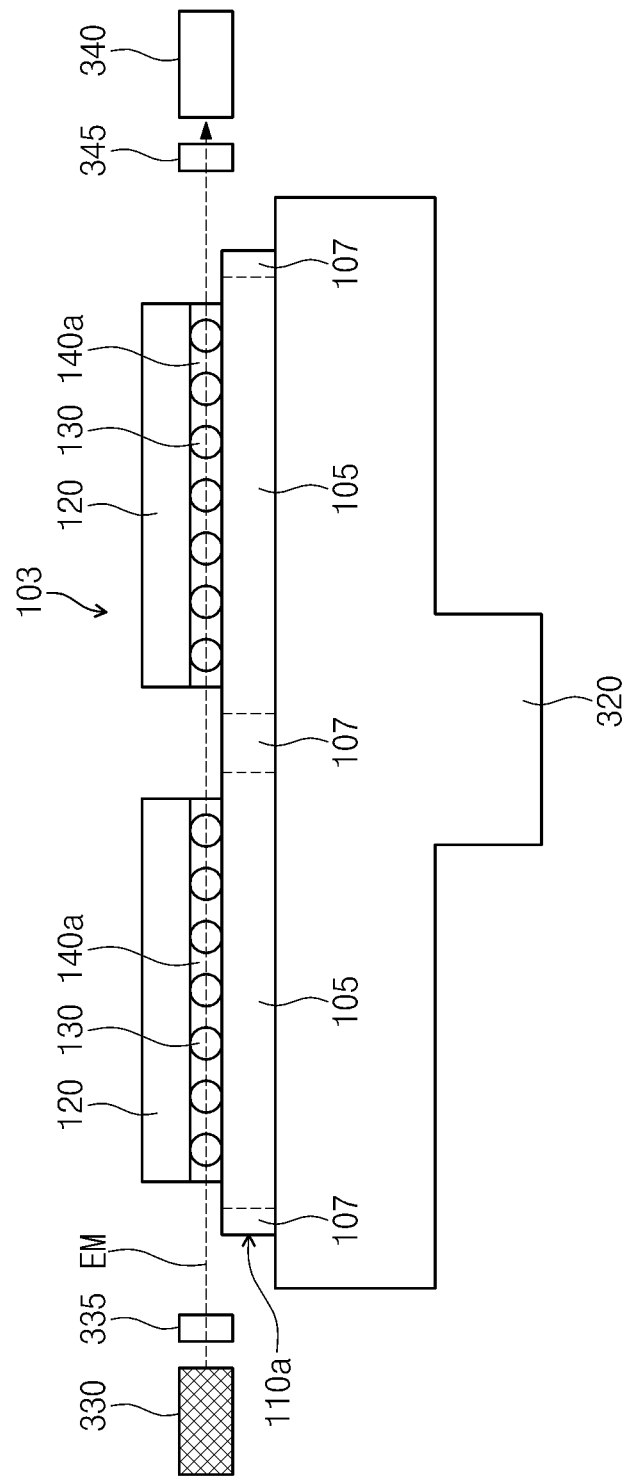
FIG. 10 is a cross-sectional view illustrating a portion of a semiconductor inspecting apparatus according to a sixth embodiment of the inventive concepts.

FIG. 10 is a cross-sectional view illustrating a portion of a semiconductor inspecting apparatus according to a sixth embodiment of the inventive concepts.

Referring to FIG. 10, a semiconductor device 103 may include a first substrate 110a including a plurality of mounting regions 105 defined by a scribe lane 107. In some embodiments, the first substrate 110a may be a semiconductor wafer including a plurality of chip regions. In this case, the plurality of chip regions may correspond to the plurality of mounting regions 105. Alternatively, the first substrate 110a may be a mother package substrate including a plurality of package regions. In this case, the plurality of package regions may correspond to the plurality of mounting regions 105.

The semiconductor device 103 may further include a plurality of second substrates 120 respectively disposed on the mounting regions 105. The second substrates 102 may be laterally spaced apart from each other. Inner terminals 130 may be disposed between each of the mounting regions 105 and each of the second substrates 120. A filling material 140 may fill a space defined between the inner terminals 130 disposed between each of the mounting regions 105 and each of the second substrates 120.

In the present embodiment, the electromagnetic wave generating unit 330 may irradiate the electromagnetic wave EM in one direction, and the electromagnetic wave EM may pass between the first substrate 110a and the second substrates 120 arranged in the one direction and may be then inputted into the electromagnetic wave detecting unit 340. The electromagnetic wave generating unit 330 and the electromagnetic wave detecting unit 340 may scan the filling materials 140 as they move in a direction perpendicular to the irradiating direction of the electromagnetic wave EM. Thereafter, at least one of the electromagnetic wave generating unit 330 and the stage 320 may be rotated, and a second scanning process may be performed using the electromagnetic wave generating unit 330 and the electromagnetic wave detecting unit 340. In a subsequent process, the first substrate 110a may be cut along the scribed lane 107 to be divided into individual semiconductor devices.

The semiconductor inspecting apparatus according to the present embodiment may inspect a plurality of semiconductor devices at the same time.

Figure 11:
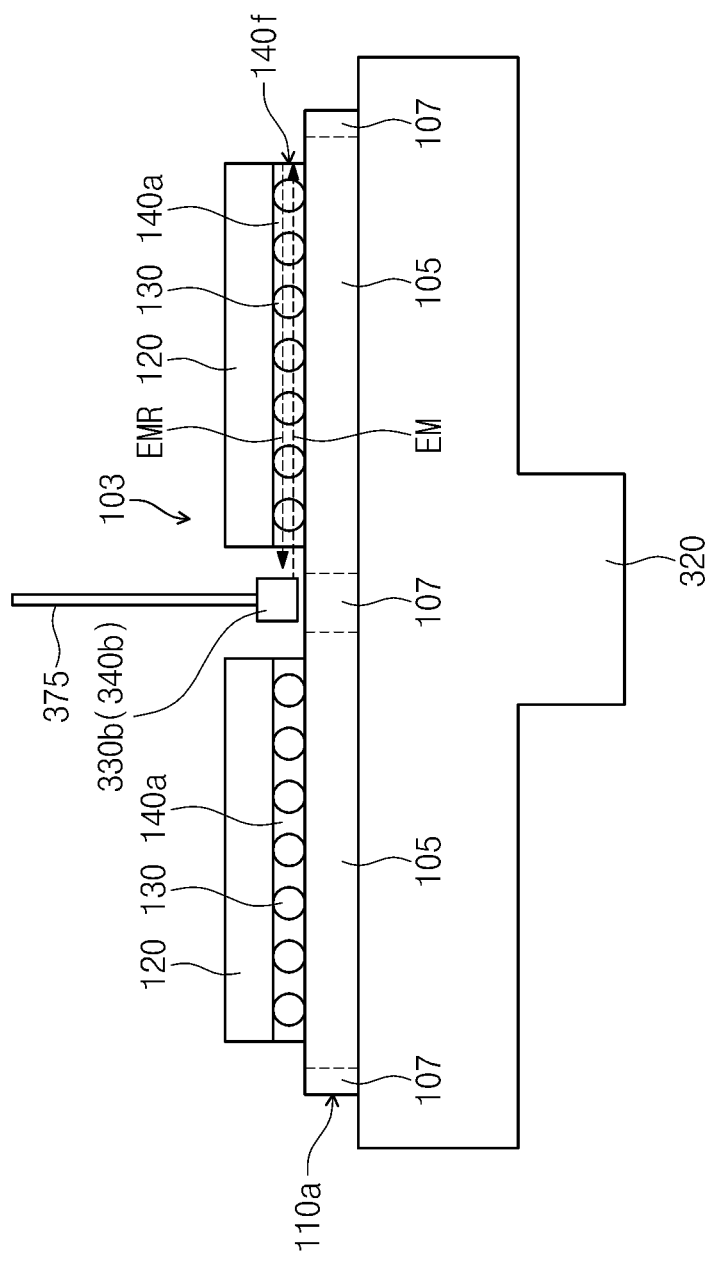
FIG. 11 is a cross-sectional view illustrating a portion of a semiconductor inspecting apparatus according to a seventh embodiment of the inventive concepts.

FIG. 11 is a cross-sectional view illustrating a portion of a semiconductor inspecting apparatus according to a seventh embodiment of the inventive concepts.

Referring to FIG. 11, an electromagnetic wave generating unit 330b and an electromagnetic wave detecting unit 340b may be combined with each other and may be loaded at a side of a filling material 140a disposed on one mounting region 105. The electromagnetic wave generating unit 330b and the electromagnetic wave detecting unit 340b combined with each other may be installed to a guide 375 to scan the filling material 140a. In some embodiments, the filling material 140a may have a first sidewall adjacent to the electromagnetic wave generating unit 330b and a second sidewall 140f opposite to the first sidewall. The scanning process may be performed using the second sidewall 140f as a reflecting surface.

In the semiconductor inspecting apparatus according to the present embodiment, the electromagnetic wave generating unit 330b and the electromagnetic wave detecting unit 340b may scan the filling material 140a on each of the mounting regions 105 along the scribe lane 107 of the first substrate 110a by the guide 375.

The aforementioned embodiments may be combined in various forms under a non-contradictable condition.

Next, a method of inspecting a semiconductor device according to some embodiments will be described with reference to FIG. 12. Hereinafter, a method of inspecting the semiconductor device 100 of FIGS. 1 to 3 will be mentioned as an example.

Figure 12:
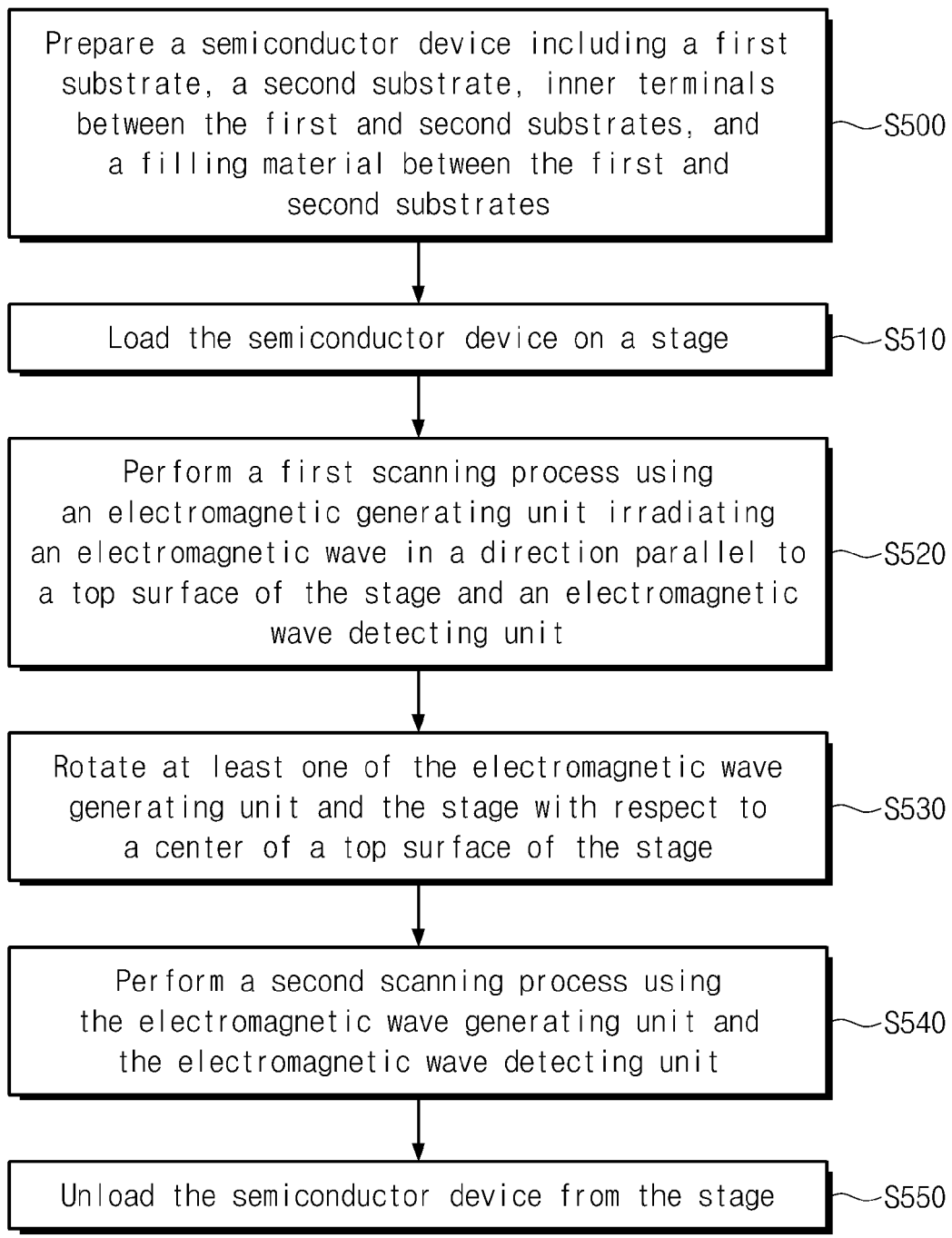
FIG. 12 is a flowchart illustrating a method of inspecting a semiconductor device according to some embodiments of the inventive concepts.

FIG. 12 is a flowchart illustrating a method of manufacturing a semiconductor device, including a method of inspecting a semiconductor device according to some embodiments of the inventive concepts.

Referring to FIGS. 1 to 3 and 12, a semiconductor device 100 is prepared (S500). The semiconductor device 100 may include a first substrate 110, a second substrate 120 stacked on the first substrate 110, and inner terminals 130 disposed between the first and second substrates 110 and 120, and a filling material disposed between the first and second substrates 110 and 120. For example, the semiconductor device 100 may be prepared by preparing a first substrate 110, preparing a second substrate 120, connecting the first substrate to second substrate via connection terminals 130 (e.g., via a heating or other process, wherein the connection terminals 130 may initially be part of one of the first or second substrates, and the connecting process results in the connection terminals being connected to (e.g., adhered to) both substrates), and depositing the filling material 140 in spaces between the first and second substrate 110 and 120. The filling material 140 may be disposed in a space between the inner terminals 130. The filling material 140 may extend to cover a sidewall of the second substrate 120. Alternatively, the filling material 140 may not cover the sidewall of the second substrate 120, as illustrated in FIG. 8.

Preparing the semiconductor device 500 may include preparing a single semiconductor device, such as, for example, a single semiconductor package including the first and second substrates 110 and 120, or a single stack of semiconductor chips including the first and second substrates 110 and 120. Alternatively, preparing the semiconductor device 500 may include preparing the first substrate 110 in a wafer form, and preparing the second substrate 120 as one of a plurality of devices (e.g., semiconductor chips) stacked on the first substrate 110 (e.g., as shown in FIGS. 10 and 11), and then connecting the first and second substrates 110 and 120 using inner connecting terminals 130, and providing a filling material 140 between the first substrate 110 and the second substrate 120 (and between the first substrate 110 and other second substrates stacked on the first substrate 110, for example, in the manner shown in FIGS. 10 and 11).

In a plan view, the inner terminals 130 may be arranged as described with reference to FIG. 2. Alternatively, the inner terminals 130 may be arranged as described with reference to FIG. 4.

The semiconductor device 100 may be loaded on the top surface of the stage 320 of the semiconductor inspecting apparatus 300 (S510).

Next, a first scanning process may be performed using the electromagnetic wave generating unit 330 and the electromagnetic wave detecting unit 340 (S520). As described with reference to FIGS. 1 to 3, the electromagnetic wave generating unit 330 may irradiate the electromagnetic wave EM in the direction parallel to the top surface of the first substrate 110. The electromagnetic wave generating unit 330 may first scan the filling material 140 as it moves in a direction that is perpendicular to the irradiating direction of the electromagnetic wave EM and is parallel to the top surface of the first substrate 110. As described above, the filling material 140 in the row-spaces between the rows of the inner terminals 130 may be inspected by the first scanning process S520. As discussed above, moving the electromagnetic wave generating unit 330 perpendicular to the irradiating direction of the electromagnetic wave EM is one example where the irradiating direction of the electromagnetic wave EM is maintained to be in a direction parallel to the longitudinal direction of the rows as the electromagnetic wave generating unit 330 is moved to consecutively traverse the rows (e.g., as it moves along a side of the semiconductor device 100). This same general description of this movement applies to instances below describing moving the electromagnetic wave generating unit 330 perpendicular to the irradiating direction of the electromagnetic wave EM.

If the inner terminals 130 are arranged as illustrated in FIG. 2, the electromagnetic wave EM may be irradiated in the second direction D2 in the first scanning process. In this case, the electromagnetic wave generating unit 330 may move in a direction (e.g., the first direction D1) perpendicular to the second direction D2. Alternatively, if the inner terminals 130 are arranged as illustrated in FIG. 4, the electromagnetic wave EM may be irradiated in the third direction D3 in the first scanning process. In this case, the electromagnetic wave generating unit 330 may move in a direction (e.g., the fourth direction D4) perpendicular to the third direction D3.

A first component (e.g., an x-component) of a two-dimensional coordinates of the void V in the filling material 140 may be obtained by the first scanning process. The control system 350 may store, process and/or display the detection data which is obtained from the electromagnetic wave detecting unit 340 in the first scanning process.

Though the above steps are described in connection with FIGS. 1-3, a similar scanning process may be used to inspect semiconductor devices in embodiments such as shown in FIGS. 10 and 11.

At least one of the electromagnetic wave generating unit 330 and the stage 320 may then be rotated with respect to a center of the top surface of the stage 320 when viewed from a plan view (S530). As described with reference to FIGS. 1 to 3, the electromagnetic wave irradiating direction of the electromagnetic wave generating unit 330 may become parallel to the columns of the inner terminals 130 by the rotation step S530.

After the rotation step S530, a second scanning process may be performed using the electromagnetic wave generating unit 330 and the electromagnetic wave detecting unit 340 (S540). As described with reference to FIGS. 1 to 3, the electromagnetic wave generating unit 330 may secondly scan the filling material 140 as it moves in a direction perpendicular to the irradiating direction of the electromagnetic wave EM. The filling material 140 in the column-spaces between the columns of the inner terminals 130 may be inspected by the second scanning process.

If the inner terminals 130 are arranged as illustrated in FIG. 2, the electromagnetic wave EM may be irradiated in the first direction D1 in the second scanning process. In this case, the electromagnetic wave generating unit 330 may move in a direction (e.g., the second direction D2) perpendicular to the first direction D1. Alternatively, if the inner terminals 130 are arranged as illustrated in FIG. 4, the electromagnetic wave EM may be irradiated in the fourth direction D4 in the second scanning process. In this case, the electromagnetic wave generating unit 330 may move in a direction (e.g., the third direction D3) perpendicular to the fourth direction D4.

A second component (e.g., a y-component) of the two-dimensional coordinates of the void V in the filling material 140 may be obtained by the second scanning process. The control system 350 may store, process and/or display the detection data which is obtained from the electromagnetic wave detecting unit 340 in the second scanning process.

The filling material 140 may be two-dimensionally scanned by the first and second scanning processes described above. As a result, if the void V exists in the filling material 140, the two-dimensional coordinates of the void V may be obtained. During each step of the scanning process, a void may be detected, for example, by comparing a physical characteristic of a detected electromagnetic wave (e.g., an intensity) with a predetermined expected amount, to determine whether there is a match. For example, as described above, in certain embodiments, if the intensity of the electromagnetic wave detected is different from (e.g., less than) an expected amount, the control system 350 may determine that a void exists in the row or column being examined.

After the second scanning process, the semiconductor device 100 may be unloaded from the stage 320 (S550). Alternatively, after the second scanning process in an embodiment such as shown in FIG. 10 or 11, the first semiconductor substrate 110a (e.g., a wafer) can be cut, and individual semiconductor devices can be singulated. In either embodiment, after semiconductor devices are unloaded from the stage 320, those that pass inspection (e.g., no voids are detected, or if voids are detected, their number or size is below a particular threshold) may be further processed (e.g., may be further encapsulated, or may be placed into an electronic device such as memory module, memory card, a larger package-on-package device, a cellular phone, a tablet, etc.). In certain embodiments, semiconductor devices that do not pass inspection may be discarded.

According to the semiconductor inspecting apparatus described above, the electromagnetic wave generating unit irradiates the electromagnetic wave between the first and second substrates to inspect the filling material, so reliability of the inspection may be improved. In addition, the electromagnetic wave generating unit scans the filling material as it moves. Thus, the semiconductor inspecting apparatus may inspect various-sized semiconductor devices, and devices for generating the electromagnetic wave may be minimized to reduce costs of the semiconductor inspecting apparatus.

While the inventive concepts have been described with reference to example embodiments, it will be apparent to those skilled in the art that various changes and modifications may be made without departing from the spirits and scope of the inventive concepts. Therefore, it should be understood that the above embodiments are not limiting, but illustrative. Thus, the scope of the inventive concepts is to be determined by the broadest permissible interpretation of the following claims and their equivalents, and shall not be restricted or limited by the foregoing description.

What is claimed is:

1. A method of manufacturing a semiconductor device, the method including:
   preparing a first substrate;
   preparing a second substrate;
   connecting the first substrate to the second substrate through interconnection terminals disposed between the first substrate and the second substrate;
   depositing a filling material in spaces between the first substrate and second substrate, the filling material filling spaces between terminals of the interconnection terminals, wherein the first substrate, second substrate, interconnection terminals, and filling material form a semiconductor device; and
   performing an inspection of the semiconductor device, the inspection including:
   loading the semiconductor device on a stage;
   irradiating an electromagnetic wave to the filling material in a first direction parallel to a top surface of the first substrate by an electromagnetic wave generator; and
   scanning the filling material by moving the electromagnetic wave generator with respect to the stage along a first side of the semiconductor device while maintaining the first irradiating direction of the electromagnetic wave EM.

2. The method of claim 1, wherein the scanning the filling material includes:
   moving the electromagnetic wave generator in a second direction perpendicular to the first irradiating direction of the electromagnetic wave.

3. The method of claim 1, wherein:
   the interconnection terminals are arranged in rows and columns, including row-spaces between the rows, and column-spaces between the columns, and
   scanning the filling material includes scanning the rows and row-spaces by maintaining the first irradiating direction of the electromagnetic wave EM to be parallel to the longitudinal direction of the rows while moving the electromagnetic wave generator with respect to the stage along the side of the semiconductor device.

4. The method of claim 3, wherein:
   the scanning includes using an electromagnetic wave detector in combination with the electromagnetic wave generator to detect electromagnetic wave characteristics as the electromagnetic wave generator moves with respect to the stage along the first side of the semiconductor device.

5. The method of claim 4, further comprising:
   rotating the stage with respect to the electromagnetic wave generator; and
   subsequently scanning the filling material by scanning the columns and column-spaces, to detect electromagnetic wave characteristics as the electromagnetic wave generator moves with respect to the stage along a second side of the semiconductor device adjacent to the first side.

6. The method of claim 5, further comprising:
   based on the scanning and subsequent scanning steps, determining whether any voids are included in the filling material.

7. The method of claim 6, further comprising:
   based on the scanning and subsequent scanning steps, determining a two-dimensional location of voids included in the filling material.

8. The method of claim 1, further comprising:
   preparing a third substrate;
   connecting the third substrate to the second substrate through additional interconnection terminals disposed between the second substrate and the third substrate; and
   depositing an additional filling material in spaces between the second substrate and third substrate, wherein:
   performing the inspection of the semiconductor device further includes:
   irradiating an electromagnetic wave to the additional filling material in the first direction parallel to the top surface of the first substrate by an additional electromagnetic wave generator; and
   scanning the additional filling material by moving the additional electromagnetic wave generator together with the electromagnetic wave generator.

9. The method of claim 1, wherein the first substrate is a wafer substrate, and further comprising:
   after the scanning, singulating the semiconductor device from the wafer.

10. A method of manufacturing a semiconductor device, the method comprising:
    preparing a semiconductor device comprising a first substrate, a second substrate disposed on the first substrate, inner terminals disposed between the first and second substrates, and a filling material disposed between the first and second substrates and between the inner terminals;
    loading the semiconductor device on a stage;
    irradiating an electromagnetic wave to the filling material in a direction parallel to a top surface of the first substrate by an electromagnetic wave generating unit; and scanning the filling material as the electromagnetic wave generating unit is moved in relation to the stage in a direction along a first side of the semiconductor device while maintaining the irradiating direction of the electromagnetic wave.

11. The method of claim 10, wherein the inner terminals are two-dimensionally arranged along rows and columns when viewed from a plan view, wherein the filling material is disposed in row-spaces between the rows and column-spaces between the columns, and wherein scanning the filling material comprises: sequentially irradiating the electromagnetic waves into the row-spaces in a direction parallel to the rows and row-spaces as the electromagnetic wave generating unit is moved along the first side of the semiconductor device.

12. The method of claim 11, wherein during the scanning, the electromagnetic wave generating unit is moved in a direction perpendicular to the irradiating direction.

13. The method of claim 11, further comprising:

rotating at least one of the electromagnetic wave generating unit and the stage with respect to a center of a top surface of the stage after sequentially irradiating the electromagnetic waves into the row-spaces; and after the rotation, sequentially irradiating the electromagnetic waves into the column-spaces as the electromagnetic wave generating unit is moved.

14. The method of claim 10, further comprising:

based on results of the scanning and the subsequent sequential irradiating steps, determining whether any voids are included in the filling material.

15. The method of claim 10, wherein:

the scanning includes using an electromagnetic wave detecting unit in combination with the electromagnetic wave generating unit to detect electromagnetic wave characteristics as the electromagnetic wave generating unit moves with respect to the stage along the first side of the semiconductor device.

16. A semiconductor inspecting method comprising:

providing a stage on which a semiconductor device is loaded, the semiconductor device comprising a first substrate, a second substrate disposed on the first substrate, inner terminals disposed between the first and second substrates, and a filling material disposed between the first and second substrates and between the inner terminals;

providing an electromagnetic wave generating unit that irradiates an electromagnetic wave to the filling material disposed between the first and second substrates in a direction parallel to a top surface of the first substrate; and providing an electromagnetic wave detecting unit that detects the irradiated electromagnetic wave, wherein the electromagnetic wave generating unit scans the filling material as the electromagnetic wave generating unit moves along a movement direction along a first side of the semiconductor device.

17. The semiconductor inspecting method of claim 16, wherein the inner terminals are two-dimensionally arranged along rows and columns when viewed from a plan view, wherein the filling material is disposed in row-spaces between the rows and column-spaces between the columns, wherein the movement direction is perpendicular to an irradiating direction of the electromagnetic wave, and wherein the electromagnetic wave generating unit sequentially irradiates the electromagnetic waves into the row-spaces as it moves.

18. The semiconductor inspecting method of claim 17, wherein at least one of the electromagnetic wave generating unit and the stage is rotated with respect to the center of the top surface of the stage after the electromagnetic wave generating unit sequentially irradiates the electromagnetic waves into the row-spaces, and wherein subsequent to the rotation, the electromagnetic wave generating unit sequentially irradiates the electromagnetic waves into the column-spaces as it moves.

19. The semiconductor inspecting method of claim 17, wherein the second substrate includes a first sidewall extending in a first direction and a second sidewall extending in a second direction intersecting the first direction, and wherein the rows are parallel to the first sidewall, and the columns are parallel to the second sidewall.

20. The semiconductor inspecting method of claim 17, wherein the second substrate includes a first sidewall extending in a first direction and a second sidewall extending in a second direction intersecting the first direction, wherein the rows are parallel to a third direction that is non-parallel to the first and second sidewalls, and wherein the columns are parallel to a fourth direction that is non-parallel to the first and second sidewalls and intersects the third direction.

\* \* \* \* \*